(12) United States Patent
Ricci et al.

(10) Patent No.: US 10,041,125 B2
(45) Date of Patent: Aug. 7, 2018

(54) ASSAY FOR PREDICTIVE BIOMARKERS

(71) Applicant: Janssen Pharmaceuticals, NV, Beerse (BE)

(72) Inventors: Deborah Ricci, Ringoes, NJ (US); Jayaprakash Karkera, Germantown, MD (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/207,879

(22) Filed: Mar. 13, 2014

(65) Prior Publication Data

US 2014/0271631 A1    Sep. 18, 2014

Related U.S. Application Data

(60) Provisional application No. 61/793,133, filed on Mar. 15, 2013.

(51) Int. Cl.
 *A61K 31/573* (2006.01)
 *C12Q 1/6886* (2018.01)

(52) U.S. Cl.
 CPC ..... *C12Q 1/6886* (2013.01); *C12Q 2600/106* (2013.01); *C12Q 2600/156* (2013.01); *C12Q 2600/158* (2013.01)

(58) Field of Classification Search
 None
 See application file for complete search history.

(56) References Cited

U.S. PATENT DOCUMENTS

| | | | |
|---|---|---|---|
| 6,638,727 | B1 | 10/2003 | Hung et al. |
| 2006/0240450 | A1 | 10/2006 | Ralph et al. |
| 2007/0065859 | A1 | 3/2007 | Wang et al. |
| 2007/0212702 | A1 | 9/2007 | Tomlins et al. |
| 2008/0081037 | A1 | 4/2008 | Grosse et al. |
| 2009/0023136 | A1 | 1/2009 | Weinshilboum et al. |
| 2010/0068802 | A1* | 3/2010 | Qiu .............. C07K 14/721 435/325 |
| 2010/0120788 | A1 | 5/2010 | Wang et al. |
| 2011/0097717 | A1 | 4/2011 | Bankaitis-Davis |
| 2011/0110926 | A1 | 5/2011 | Luo et al. |
| 2013/0064881 | A1* | 3/2013 | Nemunaitis ........... A61K 9/127 424/450 |
| 2015/0233927 | A1* | 8/2015 | Giannakakou ... G01N 33/57434 514/449 |

FOREIGN PATENT DOCUMENTS

| | | |
|---|---|---|
| JP | 2002535628 A | 10/2002 |
| JP | 2005532780 A | 11/2005 |
| JP | 2006166823 A | 6/2006 |
| JP | 2006526383 A | 11/2006 |
| JP | 2006526383 A5 | 11/2006 |
| JP | 2009507492 A | 2/2009 |
| JP | 2009509502 A | 3/2009 |
| JP | 2010517510 A | 5/2010 |
| JP | 2011514522 A | 5/2011 |
| WO | 2005100606 A2 | 10/2005 |
| WO | 2008086342 A2 | 7/2008 |
| WO | 2009009432 A2 | 1/2009 |
| WO | WO 2009/108637 A1 | 9/2009 |
| WO | WO 2011/057064 A1 | 5/2011 |
| WO | WO 2012116294 A1 | 8/2012 |

OTHER PUBLICATIONS

E. Efstathiou, et al.: "Effects of Abiraterone Acetate on Androgen Signaling in Castrate-Resistant Prostate Cancer in Bone", Journal of Clinical Oncology, vol. 30, No. 6, Dec. 19, 2011, pp. 637-643, XP055139375.

Zhu, Xiang, et al., "Identification of an Exon 3 Deletion Splice Variant Androgen Receptor mRNA in Human Breast Cancer", Int. J. Cancer, (1997), vol. 72, pp. 574-580.

* cited by examiner

*Primary Examiner* — Michael Pak

(57) ABSTRACT

The present invention provides assays for detecting presence or quantity of multiple biomarkers in one biological sample.

1 Claim, No Drawings

SEQUENCE LISTING

```
<160> NUMBER OF SEQ ID NOS: 24

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tgcagcctat tgcgag                                                    16

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcttctacca gctcaccaag ct                                             22

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gattagcagg tcaaaagtga actgat                                         26

<210> SEQ ID NO 4
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
actctgggag cagct                                                     15

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggaaatgtt atgaagcagg ga                                             22

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caaacaccct caagattctt tcaga                                          25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ctgggagaaa aattccgggt                                                20

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggaaatgtta tgaagcaggg atg                                            23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttgagatgc ttgcaattgc c                                              21

<210> SEQ ID NO 10
<211> LENGTH: 18
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
cttgcctgat tgcgagag                                                 18

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgggagaga gacagcttgt acac                                          24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caggtcaaaa gtgaactgat gca                                           23

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
cggcaggaag cctctat                                                  16

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gagctaagca ggaggcgga                                                19

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
taggcacact caaacaacga ctg                                           23

<210> SEQ ID NO 16
<211> LENGTH: 19
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 16
ttgaactcac tcaggtacc                                                 19

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tacctatcat tactcgatgc tgttga                                         26

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctggtacaaa ctgctcatca ttgtc                                          25

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
ccacaaaacc aagcgag                                                   17

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gccaccgtgc gaggtat                                                   17

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caccatccgc tttttcttgt c                                              21

<210> SEQ ID NO 22
<211> LENGTH: 15
<212> TYPE: DNA
<213> ORGANISM: Artificial Sequence

```
-continued

<220> FEATURE:
<223> OTHER INFORMATION: Description of Artificial Sequence: Synthetic
      probe

<400> SEQUENCE: 22
ccacaagctg aaggc                                                       15

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcggattctc atggaacaca                                                  20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggtcagccag gagcttcttg                                                  20
```

ASSAY FOR PREDICTIVE BIOMARKERS

CROSS REFERENCE TO RELATED APPLICATIONS

This application claims priority to U.S. Patent Application Ser. No. 61/793,133, filed Mar. 15, 2013, the contents of which are incorporated by reference herein in its entirety for all purposes.

SEQUENCE LISTING

The instant application contains a Sequence Listing which has been submitted electronically in ASCII format and is hereby incorporated by reference in its entirety. Said ASCII copy, created on Apr. 14, 2014, is named PRD3300USNP_SL.txt and is 5,686 bytes in size.

FIELD OF THE INVENTION

The invention is related to an assay for determining and detecting biomarkers and methods of treatment of cancer patients.

BACKGROUND OF THE INVENTION

While advances in development of successful cancer therapies progress, only a subset of patients respond to any particular therapy. With the narrow therapeutic index and the toxic potential of many available cancer therapies, such differential responses potentially contribute to patients undergoing unnecessary, ineffective and even potentially harmful therapy regimens.

One way to optimize therapy to treat individual patients is to determine whether one or more predictors correlate with a particular outcome in response to therapy. The ability to predict drug sensitivity in patients is particularly challenging because drug responses reflect both the properties intrinsic to the target cells and also a host's metabolic properties.

There is a need to identify further predictive markers to identify particular cancer patients who are expected to have a favorable outcome when administered particular cancer therapies. There is also a further need to identify assays useful for determining presence of more than one biomarker in a sample at once.

SUMMARY OF THE INVENTION

The invention provides a method for determining the presence, absence or quantity of more than one biomarker in a biological sample.

The invention also provides a method for treating a patient who has an increased chance for a favorable outcome in response to a cancer treatment, comprising: determining the presence, absence or quantity of one or more predictors in the patient, wherein the presence, absence or quantity of the predictor correlates with at least one favorable outcome; and based on the presence, absence or quantity of the predictor, administering a treatment to the patient.

DETAILED DESCRIPTION OF THE INVENTION

The present inventors have discovered gene expression assays useful to detect and quantitate more than one biomarker at once in a biological sample. Such biomarkers may be used to identify patients who are: at increased risk of developing a disease; increased risk of poor prognosis; increased chance of positive prognosis; likely to display a favorable outcome in response to a particular treatment; or likely to display an unfavorable outcome in response to a particular treatment.

Without limitation, the present invention provides (a) methods for predicting response to a treatment in a cancer patient by determining presence or quantity of one or more predictors, (c) methods for treating cancer by selecting patients based on presence or quantity of one or more predictors and (d) treating cancer in patients based on the patient's biomarker profile.

In certain embodiments, a method is provided for predicting response to a cancer treatment (for example, treatment with a CYP17 inhibitor such as abiraterone or a pharmaceutically acceptable salt thereof) in a cancer patient comprising determining the presence or quantity of a predictor in a patient or a biological sample from the patient; and wherein the presence or quantity of the predictor is correlated with at least one positive outcome. Certain embodiments comprise determining the presence or quantity of a second predictor in the patient or a biological sample from the patient, wherein the presence or quantity of the second predictor is correlated with at least one positive outcome.

The present invention involves the identification of predictors also referred to herein as "variants", "markers" "biomarkers" and/or "factors", that correlate with an increased probability of favorable response to a cancer treatment. The association of patient response to a cancer treatment with these predictors can increase higher confidence in the safety and/or efficacy with the particular treatment. The predictors may be a gene, protein, patient characteristic, or aspect of the patient history.

Predictors according to this invention and useful in the assay of the invention include: full length androgen receptor (AR); AR variant 1 (ARV1), AR Variant 3/Variant 7 (ARV3/V7), AR Variant 567 (ARV567), AR variant 8 (ARV8), TMPRSS2 full length wide type; ERG full length wild type; ETV1 full length wild type; TMPRSS2:ETV1 fusion gene (TMP:ETV); and TMPRSS2:ERG fusion gene (TMP:ERG); CYP17; CYP11; HSD3B1; AKRIC3; NPY; PSA; KLK2; AGR2; BST1; PTPRC; and the SNPs L701H, H974Y, T877A, V715M; ESR1; Her2; Estrogen receptor (ER); PR; CYP19, and Delta3AR.

The assay of the invention detects more than one biomarker in the biological sample, and may detect any combination of biomarkers in a sample. In one embodiment, the assay detects TMP:ERG and one or more biomarkers selected from the group consisting of AR, ARV1, ARV3/V7, ARV567, ARV8, TMPRSS2, ERG, ETV and TMP:ETV.

As used herein, the terms "comprising", "containing", "having" and "including" are used in their open, non-limiting sense.

"Quantity" may mean the value, intensity, concentration, amount, degree, or expression level. For example, quantity of a gene may be the number of times a gene or portion thereof is present in a subject's genome or in the cells of the subject. Quantity may also mean the number of cells in a biological sample expressing a marker, or the overall expression level or intensity of the marker in a biological sample. Quantity may also refer to the number of types or lines of therapy the patient to which the patient may previously been exposed. The quantity may be in comparison to an absolute number, in comparison to a reference sample from a healthy patient, in comparison to an average number from healthy patients, or in comparison to an average number from patients with similar disease.

The cancer treatment may include administration of a single drug or treatment, or a combination treatment comprising administration of more than one drug or treatment. The cancer treatment may be administration of chemotherapy, radiotherapy, or immunotherapy; or the cancer treatment may be a bone marrow transplant.

In certain embodiments, the cancer treatment comprises administering a CYP17 inhibitor to a patient. In some embodiments, the CYP17 inhibitor is abiraterone or a pharmaceutically acceptable salt thereof, particularly abiraterone acetate.

In certain embodiments, the cancer treatment comprises treatment with anti-cancer agents, including but not limited to, acemannan, aclarubicin, aldesleukin, alemtuzumab, alitretinoin, altretamine, amifostine, aminoglutethimide, amsacrine, anagrelide, anastrozole, ancestim, asparaginase, bevacizumab, bexarotene, broxuridine, capecitabine, celmoleukin, cetrorelix, cetuximab, cladribine, clofarabine, clotrimazole, daclizumab, dexrazoxane, dilazep, docosanol, doxifluridine, bromocriptine, carmustine, cyclophosphamide, cytarabine, diclofenac, edelfosine, edrecolomab, eflornithine, emitefur, exemestane, exisulind, fadrozole, filgrastim, finasteride, fludarabine phosphate, formestane, fotemustine, gallium nitrate, gemcitabine, glycopine, heptaplatin, hydroxyurea, ibandronic acid, imiquimod, iobenguane, irinotecan, irsogladine, lanreotide, leflunomide, lenograstim, lentinan sulfate, letrozole, liarozole, lobaplatin, lonidamine, masoprocol, melarsoprol, melphalan, mercaptopurine, methotrexate, metoclopramide, mifepristone, miltefosine, mirimostim, mitoguazone, mitolactol, mitomycin, mitoxantrone, molgramostim, nafarelin, nartograstim, nedaplatin, nilutamide, noscapine, oprelvekin, osaterone, oxaliplatin, pamidronic acid, pegaspargase, pentosan polysulfate sodium, pentostatin, picibanil, pirarubicin, porfimer sodium, prednisone, raloxifene, raltitrexed, rasburicase, rituximab, romurtide, sargramostim, sizofuran, sobuzoxane, sonermin, steroids, suramin, tasonermin, tazarotene, tegafur, temoporfin, temozolomide, teniposide, tetrachlorodecaoxide, thalidomide, thymalfasin, thyrotropin alfa, topotecan, toremifene, trastuzumab, treosulfan, tretinoin, trilostane, trimetrexate, ubenimex, valrubicin, verteporfin, vincristine, vinblastine, vindesine, and vinorelbine. In a preferred embodiment, the cancer treatment comprises rituximab. In other preferred embodiments, the cancer treatment comprises melphalin or prednisone, or a combination of melphalin and prednisone.

In certain embodiments, the cancer treatment is a combination treatment. The combination treatment may comprise treatment with a CYP17 inhibitor and another cancer treatment or anti-cancer agent. In certain embodiments, the other anti-cancer agent is a corticosteroid, e.g., prednisone.

The favorable outcome may be an overall response rate, overall survival rate, overall complete response rate, duration of response, longer time to next therapy, treatment free interval, positive response to treatment, a longer time-to-progression, longer term survival and/or longer progression-free survival. The favorable outcome may be dose-dependent or dose-independent. The favorable outcome may be in comparison to no treatment, or in comparison to another cancer treatment or cancer treatment(s).

"Cancer" or "tumor" is intended to include any neoplastic growth in a patient, including an initial tumor and any metastases. The cancer can be of the hematological or solid tumor type. Hematologic cancers include such as myelomas e.g., multiple myeloma), leukemias (e.g., Waldenstrom's syndrome, acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large B cell lymphoma, malignant lymphoma, plasmocytoma, reticulum cell sarcoma, Hodgkin's disease, non-Hodgkin's lymphoma or follicular B-cell non-Hodgkin's lymphoma). Solid tumors can originate in organs, and include cancers such as brain, skin, lung, breast, prostate, ovary, colon, kidney, and liver. The cancer may be at the primary site, a metastasis, refractory (e.g., refractory to one or more lines of treatment) and/or recurring. In certain embodiments, the cancer is prostate cancer or breast cancer.

When the predictor is present within the patient's body, the presence, absence or quantity of the predictor may be assessed by obtaining a biological sample from a patient and determining whether said biological sample contains the predictor or in what amounts the biological sample contains the predictor. A "biological sample" as used herein refers to a sample containing or consisting of tissues, cells, biological fluids and isolates thereof, isolated from a subject, as well as tissues, cells and fluids present within a subject. Examples of biological samples include, for example, sputum, blood, blood cells (e.g., white blood cells), amniotic fluid, plasma, serum, semen, saliva, bone marrow, tissue or fine-needle biopsy samples, urine, peritoneal fluid, pleural fluid, and cell cultures. Biological samples may also include sections of tissues such as frozen sections taken for histological purposes. In certain embodiments, the biological sample may be or include tumor cells. In certain embodiments, the biological sample may be formalin fixed. In certain embodiments, the biological sample may be circulating tumor cells.

Detection of predictor in a biological sample may be performed by any conventional method for detecting the type of predictor, e.g., direct measurement, immunohistochemistry, immunoblotting, immunofluorescence, immunoabsorbence, immunoprecipitations, protein array, fluorescence in situ hybridization, FACS analysis, hybridization, in situ hybridization, Northern blots, Southern blots, Western blots, ELISA, radioimmunoassay, gene array/chip, PCR, RT-PCR, or cytogenetic analysis.

When the predictor is based on a particular genotype or polymorphism, the biological sample may be analyzed by genotyping. The term "genotype" refers to the alleles present in DNA from a subject or patient, where an allele can be defined by the particular nucleotide(s) present in a nucleic acid sequence at a particular site(s). Often a genotype is the nucleotide(s) present at a single polymorphic site known to vary in the human population. "Genotyping" refers to the process of determining the genotype of an individual by the use of biological assays. Current methods of doing this include PCR, DNA sequencing, antisense oligonucleotide probes, and hybridization to DNA microarrays or beads.

A "single nucleotide polymorphism" (SNP, pronounced snip) is a DNA sequence variation occurring when a single nucleotide—A, T, C, or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case it is said that there are two alleles: C and T. Almost all common SNPs have only two alleles.

The detection of the presence or absence of at least one genotype variance involves contacting a nucleic acid sequence corresponding to one of the genes identified herein or a product of such a gene with a probe. The probe is able to distinguish a particular form of the gene or gene product or the presence or a particular variance or variances, e.g., by differential binding or hybridization.

When the predictor is the presence or quantity (including the expression level) of a particular gene or protein, the presence or quantity (including the expression level) may be determined by immunohistochemistry of a biological sample.

In certain embodiments, a method for treating a patient for cancer comprising: determining the presence or quantity of a first predictor in patient or a biological sample from said patient; and determining the presence or quantity of a second predictor in said patient or a biological sample from said patient; and selecting a method of treatment dependent on whether said patient is likely to respond to said treatment.

The invention also provides uses of CYP17 inhibitors for the treatment of cancer in a patient, where the patient is characterized by the presence, absence, or quantity of at least one predictor correlated with at least one positive outcome in response to the CYP17 inhibitor.

All publications cited herein are hereby incorporated by reference. Unless defined otherwise, all technical and scientific terms used herein have the same meaning as commonly understood to one of ordinary skill in the art to which this invention pertains.

Example 1

TaqMan qRT-PCR assays were developed to evaluate the presence of several previously identified AR splice variants, including ARV1, ARV3/V7, ARV567 and ARV8, AR somatic mutations, including L701H, V715M, H874Y and T877A, along with TMPRSS2 fusion genes, TMPRSS2: ERG and TMPRSS2:ETV1, in two independent PCa FFPET sample sets. The first sample set consisted of 42 prostate adenocarcinomas ranging from stage II to stage IV. Results showed that ARV1 and ARV3/V7 were the most prevalent variants with 92% of all samples showing expression of either or both variant. TMPRSS2:ERG was present in 72% of all samples tested, with a high concordance to AR variant expression, prevalent in later stage (III/IV) PCa samples. The second sample set consisted of 8 prostate adenocarcinomas, including matched adjacent normal FFPET. Similar expression of the AR variants was observed in both the tumor and matched normal samples, however tumor prostate samples showed a higher and more prevalent expression (66.67%) of the TMPRSS2:ERG fusion gene than in the matched normal samples (33%). None of the four AR mutations evaluated were detected in either sample set.

TABLE 1

Primers used in Example 1.

| Abbreviation | TaqMan Reporter | Probe Sequences | Forward Primer | Reverse Primer 5'-3' |
|---|---|---|---|---|
| ARFULL | VIC | TGCAGCCTATT GCGAG (SEQ ID NO: 1) | GCTTCTACCAGCTC ACCAAGCT (SEQ ID NO: 2) | GATTAGCAGGTCAA AAGTGAACTGAT (SEQ ID NO: 3) |
| ARV1 | FAM | ACTCTGG GAGCAGCT (SEQ ID NO: 4) | CGGAAATGTT ATGAAGCAGGGA (SEQ ID NO: 5) | CAAACACCCTC AAGATTCTTTCAGA (SEQ ID NO: 6) |
| ARV3/7 | FAM | CTGGGAG AAAAATTCCGG GT (SEQ ID NO: 7) | GGAAATGTTA TGAAGCAGGGATG (SEQ ID NO: 8) | TTTGAGATGCT TGCAATTGCC (SEQ ID NO: 9) |
| ARV567 | FAM | CTTGCCT GATTGCGAGAG (SEQ ID NO: 10) | CTGGGAGAGA GACAGCTTGTACAC (SEQ ID NO: 11) | CAGGTCAAAA GTGAACTGATGCA (SEQ ID NO: 12) |
| TMP:ERG | VIC | CGGCAGGAAG CCTTAT (SEQ ID NO: 13) | GAGCTAAGCAGGA GGCGGA (SEQ ID NO: 14) | TAGGCACACTCAAA CAACGACTG (SEQ ID NO: 15) |
| TMP:ETV | FAM | TTGAACTCACT CAGGTACC (SEQ ID NO: 16) | TACCTATCATTACT CGATGCTGTTGA (SEQ ID NO: 17) | CTGGTACAAACTGC TCATCATTGTC (SEQ ID NO: 18) |

Prostate Cancer Related Gene Assays

| Assay ID (Life Technologies) | Target | Abbreviation | TaqMan Reporter |
|---|---|---|---|
| hs00897322_g1 | CYP11 | CYP11 | FAM |
| hs00356521_m1 | AGR2 | AGR2 | FAM |
| hs00173470_m1 | NPY | NPY | FAM |
| hs00894732_m1 | PTPRC | PTPRC | FAM |
| hs00426435_m1 | HSD381 | HSD381 | FAM |
| hs00428383_m1 | KLK2 | KLK2 | FAM |

TABLE 1 -continued

| | | | |
|---|---|---|---|
| hs02576345_m1 | KLK3 | KLK3 | FAM |
| hs00174709_m1 | BST1 | BST1 | FAM |
| h01124136_m1 | CYP17 | CYP17 | FAM |

| Target | TaqMan Reporter | Probe Sequences | Forward Primer | Reverse Primer 5'-3' |
|---|---|---|---|---|
| RPL13A | FAM | CCACAAAA CCAAGCGAG (SEQ ID NO: 19) | GCCACCGTG CGAGGTAT (SEQ ID NO: 20) | CACCATCCGC TTTTTCTTGTC (SEQ ID NO: 21) |
| RPL19 | VIC | CCACAAGC TGAAGGC (SEQ ID NO: 22) | GCGGATTCTC ATGGAACACA (SEQ ID NO: 23) | GGTCAGCCA GGAGCTTCTTG (SEQ ID NO: 24) |

Example 2

Using TaqMan qRT-PCR 213 female breast-cancer FFPET samples were examined, 80 ER− PR− Her2− samples, 68 ER− PR− Her2+ samples, and 64 ER+ PR+ Her2− samples, as well as 8 breast-cancer cell lines for the presence of ESR1, CYP17, CYP19, full length AR and AR splice variants ARV1, ARV3/V7, ARV567, and Delta3AR. ARV3/V7 and Delta3AR were the most prevalent variants in the ER+ PR+ Her2− and ER− PR− Her2+ sample sets, with >85% of these samples showing expression of either or both of these variants. On the other hand, ARV1, ARV3/V7, and ARV567 were the most prevalent variants in the ER− PR− Her2-sample set, with >90% of these samples showing expression of one or a combination of these variants. Lower expression values of most of the AR variants were observed in higher grade ER+ PR+ Her2− and ER− PR− Her2+ samples as compared to the lower grade samples. CYP19 was highly prevalent in all sample sets with >75% of all samples showing expression, while CYP17 expression was observed in <30% of all the samples tested.

The invention claimed is:

1. A method for treating a prostate cancer in a patient comprising:
   a. obtaining a biological sample from the patient;
   b. testing the biological sample for multiple biomarkers using an assay that detects TMPRSS2:ERG fusion gene (TMP:ERG) and at least one biomarker selected from the group consisting of full length androgen receptor (AR), AR variant 1 (ARV1), AR variant 3/variant 7 (ARV3/V7), AR variant 576 (ARV567), AR variant 8 (ARV8), TMPRSS2 full length wild type, ERG full length wild type, ETV1 full length wild type, TMPRSS2:ETV1 fusion gene (TMP:ETV) and detecting the presence, absence or quantity of such biomarkers;
   c. based on the presence of TMPRSS2:ERG fusion gene (TMP:ERG), and the presence, absence or quantity of the at least one biomarker in such biological sample, selecting a patient likely to display a favorable outcome in response to treatment with a safe and effective amount of abiraterone acetate and prednisone to treating the prostate cancer by administering the abiraterone acetate and prednisone to the patient.

* * * * *